US00PP37703P3

(12) United States Plant Patent
Schwartz

(10) Patent No.: US PP37,703 P3
(45) Date of Patent: Sep. 15, 2026

(54) ***ZOYSIA JAPONICA* PLANT NAMED '16-TZ-14114'**

(50) Latin Name: *Zoysia japonica*
Varietal Denomination: 16-TZ-14114

(71) Applicants: University of Georgia Research Foundation, Inc., Athens, GA (US); Patten Seed Company, Fort Valley, GA (US)

(72) Inventor: Brian Schwartz, Tifton, GA (US)

(73) Assignees: University of Georgia Research Foundation, Inc., Athens, GA (US); Patten Seed Company, Fort Valley, GA (US)

( * ) Notice: Subject to any disclaimer, the term of this patent is extended or adjusted under 35 U.S.C. 154(b) by 0 days.

(21) Appl. No.: 19/052,226

(22) Filed: Feb. 12, 2025

(65) Prior Publication Data

US 2025/0261572 P1 Aug. 14, 2025

Related U.S. Application Data

(60) Provisional application No. 63/101,186, filed on Feb. 12, 2024.

(51) Int. Cl.
*A01H 5/12* (2018.01)
*A01H 6/46* (2018.01)

(52) U.S. Cl.
USPC ..... Plt./390

(58) Field of Classification Search
USPC ..... Plt./384, 390
See application file for complete search history.

(56) References Cited

PUBLICATIONS

Braun et al. 2021. Performance and playability of experimental low-impact coarse-textured zoysiagrass in multiple climates. Grass Research 1(10), pp. 1-12.*

* cited by examiner

*Primary Examiner* — Karen M Redden
(74) *Attorney, Agent, or Firm* — Thomas | Horstemeyer LLP

(57) ABSTRACT

A new and distinct plant of *Zoysia* plant named '16-TZ-14114', characterized by its wide leaf texture and vigorous growth, which results in fast establishment after planting. The *Zoysia* plant named '16-TZ-14114' is an asexually reproduced, tetraploid plant is reliably propagated vegetatively, although it is not seed or pollen sterile.

3 Drawing Sheets

Genus and species: Latin name: *Zoysia japonica.*

Variety denomination: Variety denomination: '16-TZ-14114'.

BACKGROUND OF THE INVENTION

The present invention relates to a new and distinct plant of zoysiagrass, botanically known as *Zoysia japonica*, and hereinafter referred to by the plant name '16-TZ-14114'.

The new *Zoysia* plant '16-TZ-14114' was collected and evaluated as a product of a breeding program conducted by the inventor in Tifton, Georgia. The objective of the zoysiagrass breeding program is to create new plants with improved commercial qualities, e.g., that have wide leaf texture and vigorous growth, which results in fast establishment after planting. This plant is commercially important for its excellent turfgrass quality, increased seed head production, increased nematode resistance, and other qualities, which are enumerated herein.

BRIEF SUMMARY OF THE INVENTION

The new *Zoysia* plant '16-TZ-14114' has not been observed under all possible environmental conditions. The phenotype may vary somewhat with variations in environment and cultural practices such as temperature, water and fertility levels, soil types, and light intensity without, however, any variance in genotype. The following traits have been repeatedly observed and are determined to be the unique and distinguishing characteristics of the new *Zoysia* plant '16-TZ-14114'. In combination, these traits set '16-TZ-14114' apart from all other existing varieties of *Zoysia* known to the inventor.

'16-TZ-14114' is a *Zoysia japonica* turfgrass that exhibits fast establishment (Table 1), vigorous growth and quick recovery, and wide leaf texture (Table 2). These characteristics make it an ideal turfgrass for lawns, commercial landscapes, and roadsides.

TABLE 1

Percent green plot coverage for select zoysiagrass plants during field establishmentas measured each month during 2021 in in Tifton, GA.

| | Mar | | Apr | | May | | June | | July | |
|---|---|---|---|---|---|---|---|---|---|---|
| '16-TZ-14114' | 1.5 | a | 6.6 | a | 26.3 | a | 32.7 | a | 61.2 | a |
| 'Diamond' (U.S. PP10636P) | 0.4 | b | 2.2 | b | 8.8 | b | 24.1 | ab | 58.6 | a |
| 'Palisades' (U.S. PP11515) | 0.2 | b | 0.9 | b | 7.6 | b | 12.9 | b | 42.1 | a |

TABLE 1-continued

Percent green plot coverage for select zoysiagrass plants during field establishmentas measured each month during 2021 in in Tifton, GA.

| | Mar | | Apr | | May | | June | | July | |
|---|---|---|---|---|---|---|---|---|---|---|
| 'Zeon' (U.S. PP13166) | 0.1 | b | 0.3 | b | 4.8 | b | 10.9 | b | 38.7 | a |

Means followed within columns by the same letter are not significantly different at K = 100 (approximately P = 0.05) according to the Waller-Duncan LSD.

TABLE 2

Leaf measurements of selected zoysiagrass plants measured under greenhousenconditions during 2020 in Tifton, GA.

| Genotype | Leaf width (mm) | |
|---|---|---|
| 'SS-500' Empire ™ (U.S. PP11466) | 4.12 | a |
| '16-TZ-14114' | 4.11 | a |
| 'Meyer' (not patented) | 3.38 | b |
| 'Zeon' (U.S. PP13166) | 2.07 | c |
| 'BA-305' Emerald ™ (U.S. PP18415) | 1.89 | cd |
| 'Diamond' (U.S. PP10636P) | 1.68 | d |

Means followed within columns by the same letter are not significantly different at K = 100 (approximately P = 0.05) according to the Waller-Duncan LSD.

Morphological comparisons of '16-TZ-14114' with 'Diamond', 'Emerald', 'Empire', 'Meyer', and 'Zeon' in greenhouse trials show that '16-TZ-14114' is most like 'Empire', but significantly different than 'Empire' in leaf color (Table 2), internode length (Table 3), and raceme size (Table 4). '16-TZ-14114' is significantly different from 'Meyer', 'Zeon', 'Emerald', and 'Diamond' in leaf width and length (Table 2), as well as raceme and peduncle size, and number of spikelets per raceme (Table 4). Fewer differences were observed for stolon characteristics.

BRIEF DESCRIPTION OF THE DRAWINGS

The accompanying colored photographic illustrations show the overall appearance and distinct characteristics of the new cultivar of *Zoysia japonica* '16-TZ-14114' showing the colors as true as possible. Colors in the photographs may differ slightly from the color values cited in the detailed botanical description, which accurately describes the colors of the new Genus species 'cultivar name'.

DETAILED BOTANICAL DESCRIPTION

Figure 1:
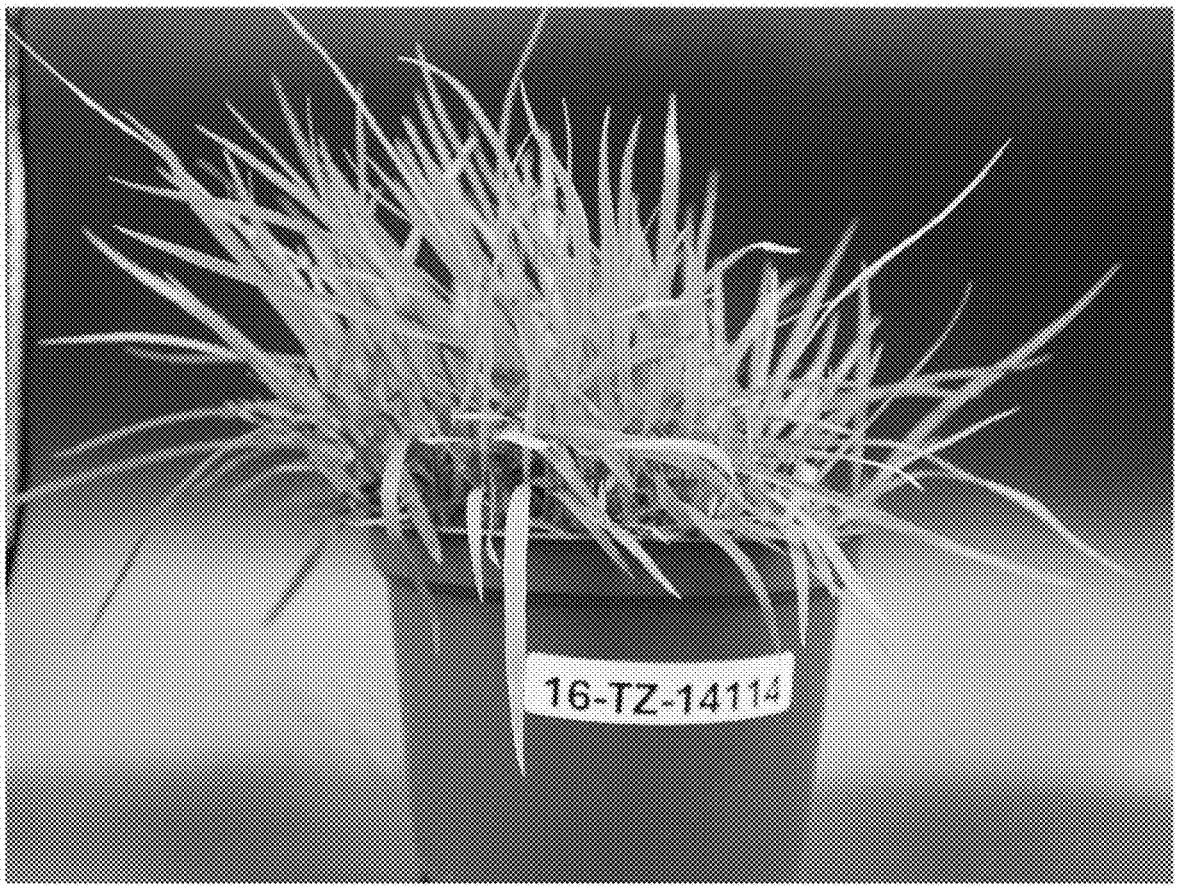
FIG. 1 is a side view of '16-TZ-14114'.
Figure 2:
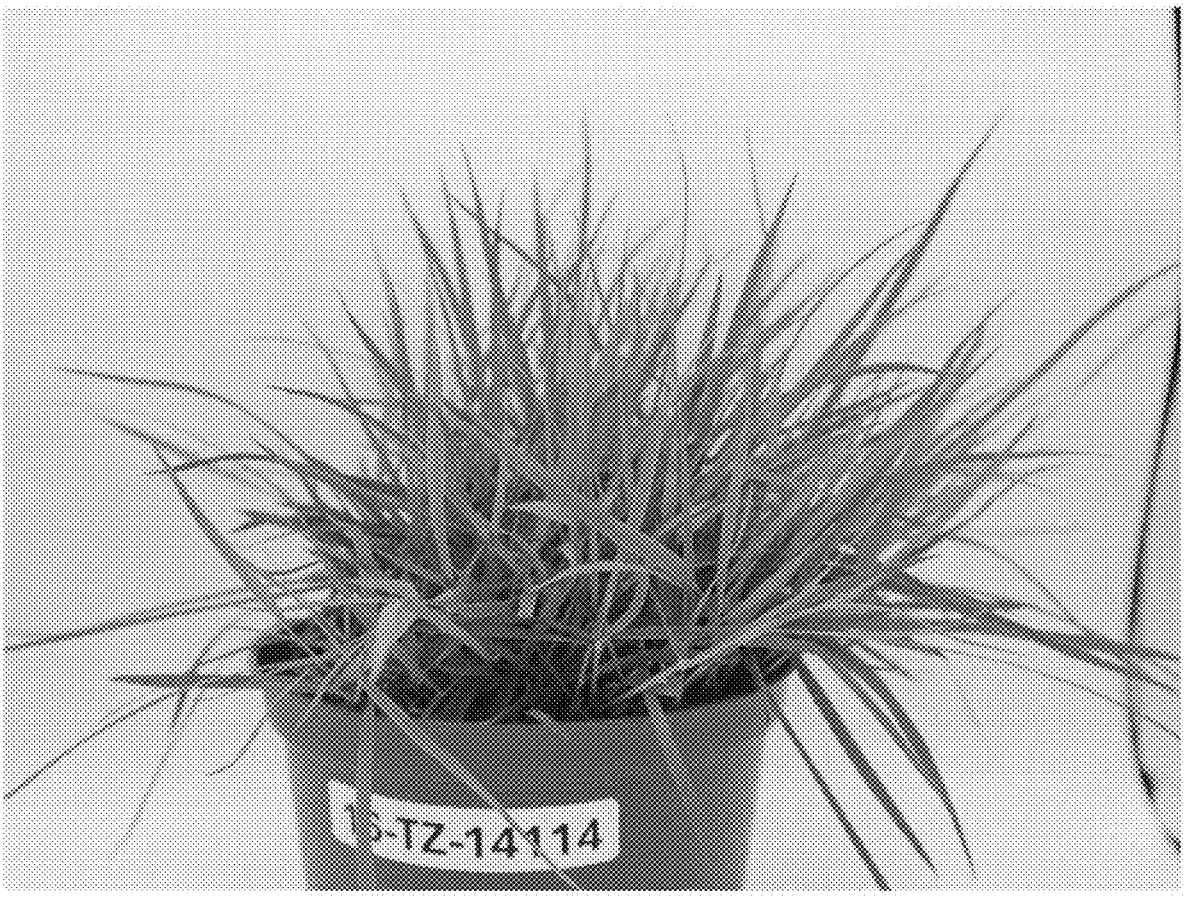
FIG. 2 is a side-view of '16-TZ-14114'.
Figure 3:
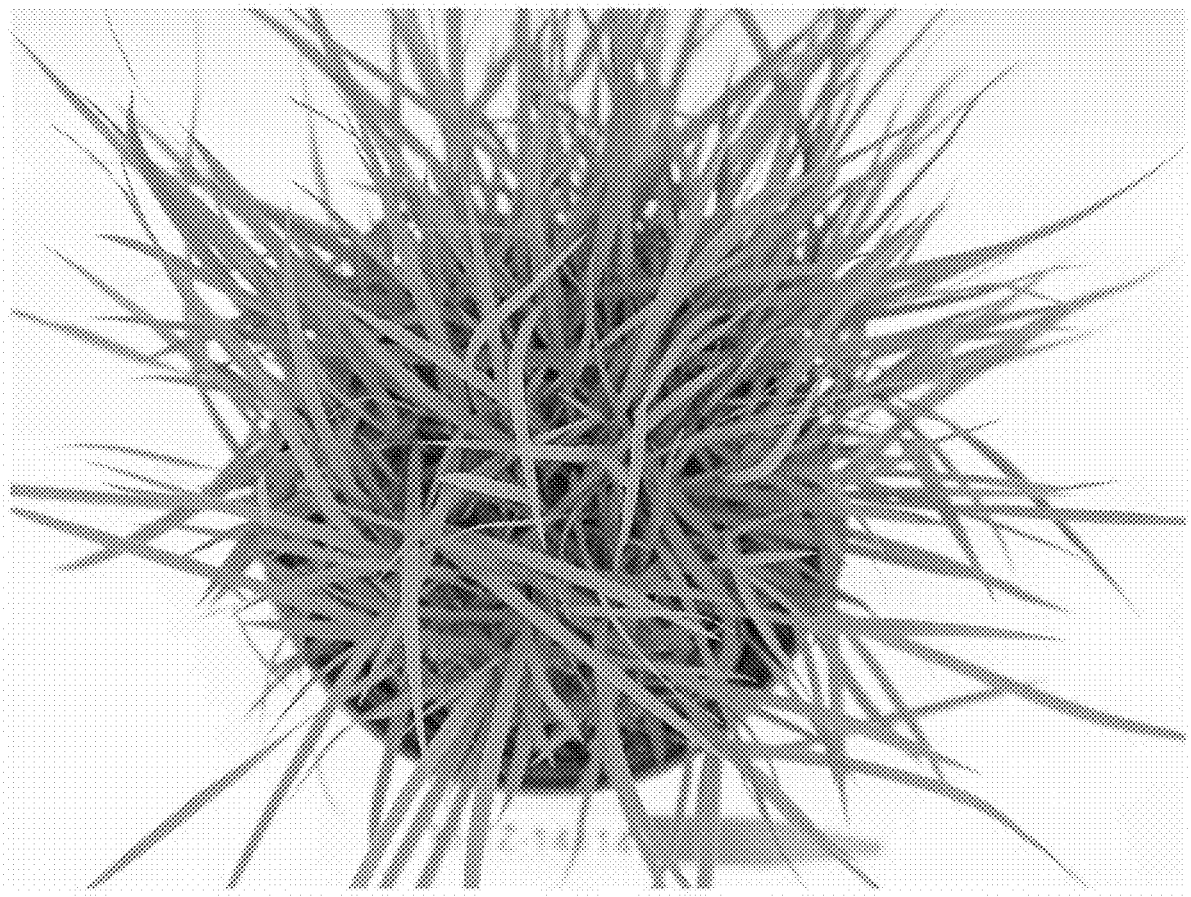
FIG. 3 is a top view of '16-TZ-14114'.

The following traits have been consistently observed in the original plant of this new variety and in asexually propagated progeny grown in Tifton, Georgia, and, to the best knowledge of the inventors, their combination forms the unique characteristics of the new variety '16-TZ-14114'. Sod, sprigs, or plugs was the type of asexual reproduction used.

The following unknown, proprietary and unpatented, parents derived from the breeding program below were used to produce the plant:

a) 2016: Selected from within an uncultivated population of mixed grasses;

b) 2016-2022: sod farm research trials for sod establishment, tensile strength, and sod re-growth;

c) 2017-Present: University research trials for general turfgrass performance;

d) 2018-Present: University research trials for winter-kill;

e) 2018-2020: University and sod farm research trials of golf rough performance;

f) 2018-2022: National Turfgrass Evaluation Program—2018 National Low Input Warm-Season Trial;

g) 2019-Present: University research trials for drought tolerance;

h) 2019-Present: Independent research trials for shade tolerance (Good Hope, GA);

The following observations, measurements, and values describe the new *Zoysia* plant '16-TZ-14114' grown in Tifton, Georgia. The following traits have been consistently observed and, to the best knowledge of the inventor, their combination forms the unique characteristics of the new variety '16-TZ-14114'. During the growing of the plants, typical day temperatures in Tifton, GA ranged from 69° F. to 99° F., and typical night temperatures ranged from 47° F. to 70° F.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England in 2007, except where general terms of ordinary dictionary significance are used.

The following observations, measurements, and values describe plants of the *Zoysia* plant '16-TZ-14114'.

'16-TZ-14114' has demonstrated quick establishment, vigorous growth, and quick recovery from injury. In field trials planted in Tifton, Georgia, plots of 'Zeon', 'Diamond', 'Palisades', and '16-TZ-14114' were evaluated for the percentage of ground covered by vegetation during each month in 2021 (Table 1). '16-TZ-14114' established rapidly and by May plots it averaged 26.3% coverage against the next highest 'Diamond' at 8.8%. In the following months during 2021, '16-TZ-14114' continued to out-grow the other plants, but the spread was not statistically faster.

The leaf of '16-TZ-14114' is wide (4.11 mm), has rolled venation, and is 77.59 mm long (Table 2). The adaxial (upper) and abaxial (lower) leaf surfaces are smooth with a few trichomes dispersed along the leaf margins. The leaf width (texture) of '16-TZ-14114' is similar to 'Empire', while significantly wider than 'Meyer', 'Zeon', 'Emerald', and 'Diamond'. The leaf color of '16-TZ-14114' most fits the Green Group 137C of The Royal Horticulture Society (R.H.S.) Colour Chart, 5$^{th}$ Edition and was also determined to have a dark green color index of 0.66 through the analysis of digital images taken under controlled lighting. This color was similar to that of 'Meyer', 'Zeon', 'Emerald', and 'Diamond', but lighter than the leaf color of 'Empire'.

The leaf sheath at the collar region of '16-TZ-14114' measured 3.56 mm ($\sigma$=0.19) and had the R.H.S. color 145B. The ligule was hairy with a 157D R.H.S. color and auricles were not pronounced. Overall stolon length of '16-TZ-14114' averaged 24.38 mm (Table 3) and had the R.H.S. color 150D. Stolon internode length for '16-TZ-14114' was 17.28 mm and was significantly shorter than found in 'Empire', while longer than those of 'Zeon', 'Emerald', or 'Diamond'.

'16-TZ-14114' has a raceme inflorescence that averaged 28.19 mm in length (Table 4) and was significantly shorter than observed on 'Empire', while being longer than those of 'Meyer', 'Zeon', 'Emerald', or 'Diamond'. '16-T-14114' peduncle length was 62.39 mm and best fit R.H.S. color 143B. Its spikelets measured 3.35 mm long (σ=0.17) and had the R.H.S. color 145D. Glumes were 0.21 mm (σ=0.02) in length with a 145D R.H.S. color, while the lemma best fit a R.H.S. color of 145C and was 0.29 mm long (σ=0.02).

Fertile Structures:

Androecium: 3 stamens, filaments slender (~4.3-4.5 mm), anthers are linear/versatile (~2.5-2.9 mm), projecting outside glumes.

Gynoecium: Small, single ovoid ovary (~0.5-0.7 mm), with 2 styles i.e. short (~2.0 mm) and 2 long feathery/plumose stigmas (~5.0-6.0 mm) that extend conspicuously during anthesis.

TABLE 3

Stolen measurements of selected zoysiagrass plants measured under greenhouse conditions during 2020 in Tifton, GA.

| Genotype | Stolon length (cm) | | Inter-node length (mm) | | Stolon internode diameter (mm) | |
|---|---|---|---|---|---|---|
| 'SS-500' Empire ™ (U.S. PP11466) | 27.05 | a | 25.52 | a | 2.47 | a |
| '16-TZ-14114' | 24.38 | ab | 17.28 | b | 2.07 | ab |
| 'Meyer' (not patented) | 23.49 | ab | 16.68 | b | 1.90 | ab |
| 'Zeon' (U.S. PP13166) | 23.31 | ab | 12.24 | c | 1.84 | a |
| 'BA-305' Emerald ™ (U.S. PP18415) | 18.68 | bc | 11.33 | c | 1.50 | ab |
| 'Diamond' (U.S. PP10636P) | 14.71 | c | 9.62 | c | 1.16 | b |

Means followed within columns by the same letter are not significantly different at K = 100 (approximately P = 0.05) according to the Waller-Duncan LSD.

TABLE 4

Inflorescence characteristics of selected zoysiagrass plants measured under greenhouse conditions during 2020 in Tifton, GA.

| Genotype | Raceme size (mm) | | Peduncle length (mm) | | Spikelets per inflo-rescence (number) | |
|---|---|---|---|---|---|---|
| 'SS-500' Empire ™ (U.S. PP11466) | 38.67 | a | 65.30 | a | 33.2 | a |
| '16-TZ-14114' | 28.19 | b | 62.39 | a | 32.0 | a |
| 'Meyer' (not patented) | 23.71 | c | 45.50 | b | 27.5 | b |
| 'Zeon' (U.S. PP13166) | 16.88 | d | 35.62 | c | 15.6 | c |
| 'BA-305' Emerald ™ (U.S. PP18415) | 12.41 | e | 18.09 | d | 15.3 | c |
| 'Diamond' (U.S. PP10636P) | 11.23 | e | 13.43 | d | 6.4 | d |

Means followed within columns by the same letter are not significantly different at K = 100 (approximately P = 0.05) according to the Waller-Duncan LSD.

TABLE 5

16-TZ-141-14 Measurements

| Task | Type | Description | AVG | SD |
|---|---|---|---|---|
| D | Color | Inflorescence peduncle | 143b | • |
| D | Color | Inflorescence floret | 145d | • |
| D | Color | Inflorescence palea | 145c | • |
| D | Color | Inflorescence lemma (fertile) | 145d | • |
| D | Color | Inflorescence lemma (sterile) | n/a | • |
| D | Color | Inflorescence glume (lower) | n/a | • |
| D | Color | Inflorescence glume (upper) | n/a | • |
| D | Color | Inflorescence awn | n/a | • |
| E | Size | Inflorescence floret | 3.345 | 0.166 |
| E | Size | Inflorescence palea | 0.288 | 0.024 |
| E | Size | Inflorescence lemma (fertile) | 0.214 | 0.019 |
| E | Size | Inflorescence lemma (sterile) | n/a | • |
| E | Size | Inflorescence glume (lower) | n/a | • |
| E | Size | Inflorescence glume (upper) | n/a | • |
| E | Size | Inflorescence awn | n/a | • |
| F | Color | Stolon | 150d | • |
| F | Color | Ligule | 157d | • |
| F | Color | Sheath | 145b | • |
| F | Color | Collar | 149d | • |
| G | Size | Sheath | 3.557 | 0.192 |
| H | Type | Ligule | hairy | • |
| — | Type | Auricle | absent | • |
| J | Type | Collar (continuous, constricted at midrib) | 0.141 | 0.033 |
| K | Descrip-tion | Upper (adaxial) leaf surface texture | smooth | • |
| K | Descrip-tion | Lower (abaxial) leaf surface texture | smooth | • |
| K | Descrip-tion | Hairs on leaf edges | few | • |
| L | Design-ation | Foliar disease | No test, assumed Bipolaris | • |
| L | Design-ation | Root disease | *Gaeuman-nomyces graminis* | • |
| M | color | Anther | 145a | • |

What is claimed is:

1. A new and distinct plant of the *Zoysia* plant named *Zoysia* '16-TZ-14114' as illustrated and described herein.

* * * * *